(12) United States Patent
Bier et al.

(10) Patent No.: US 8,649,855 B2
(45) Date of Patent: Feb. 11, 2014

(54) BURST SUPPRESSION MONITOR FOR INDUCED COMA

(75) Inventors: Michael Bier, Marina del Rey, CA (US); David A. Kaiser, Churchville, NY (US)

(73) Assignees: The Regents of the University of California, Oakland, CA (US); Wavestate, Inc., Marina Del Rey, CA (US)

( * ) Notice: Subject to any disclaimer, the term of this patent is extended or adjusted under 35 U.S.C. 154(b) by 1471 days.

(21) Appl. No.: 11/865,727

(22) Filed: Oct. 1, 2007

(65) Prior Publication Data

US 2008/0249431 A1    Oct. 9, 2008

Related U.S. Application Data

(60) Provisional application No. 60/827,433, filed on Sep. 29, 2006.

(51) Int. Cl.
     *A61B 5/04*          (2006.01)

(52) U.S. Cl.
     USPC ........................................................ 600/544

(58) Field of Classification Search
     USPC .................................. 600/544–545
     See application file for complete search history.

(56) References Cited

U.S. PATENT DOCUMENTS

| | | | |
|---|---|---|---|
| 4,566,464 A * | 1/1986 | Piccone et al. ................. | 600/545 |
| 4,788,982 A | 12/1988 | Gedeon et al. | |
| 4,846,190 A | 7/1989 | John | |
| 4,869,264 A | 9/1989 | Silberstein | |
| 5,010,891 A | 4/1991 | Chamoun | |
| 5,195,531 A | 3/1993 | Bennett | |
| 5,320,109 A | 6/1994 | Chamoun | |
| 5,792,069 A | 8/1998 | Greenwald | |
| 6,011,990 A | 1/2000 | Schultz | |
| 6,016,444 A * | 1/2000 | John ............................ | 600/544 |
| 6,067,467 A | 5/2000 | John | |
| 6,224,549 B1 | 5/2001 | Drongelen | |
| 6,231,560 B1 | 5/2001 | Bui | |
| 6,317,627 B1 * | 11/2001 | Ennen et al. .................. | 600/544 |
| 6,748,263 B2 | 6/2004 | Griffiths | |
| 7,089,927 B2 | 8/2006 | John | |
| 7,373,198 B2 | 5/2008 | Bibian | |
| 7,395,292 B2 | 7/2008 | Johnson | |
| 7,957,793 B2 * | 6/2011 | Montgomery et al. ........ | 600/544 |
| 2005/0137494 A1 * | 6/2005 | Viertio-Oja ................... | 600/544 |
| 2006/0009709 A1 | 1/2006 | Rautee | |
| 2006/0167722 A1 | 7/2006 | Mrf Struys | |
| 2006/0190044 A1 | 8/2006 | Libbus | |
| 2007/0276609 A1 * | 11/2007 | Greenwald ..................... | 702/19 |
| 2009/0048530 A1 | 2/2009 | Sarkela | |

OTHER PUBLICATIONS

Leistritz et al., "New Approaches for the Detection and Analysis of Electroencephalographic Burst-Suppression Patterns in Patients under Sedation" 1999, Journal of Clinical Monitoring and Computing, vol. 15, No. 6, pp. 357-367.*

(Continued)

*Primary Examiner* — Navin Natnithithadha
*Assistant Examiner* — Eric Messersmith
(74) *Attorney, Agent, or Firm* — Quine Intellectual Property Law Group, P.C.; Stephen J. LeBlanc

(57) ABSTRACT

Methods and systems for monitoring subjects, analyzing EEG data, and maintaining subjects at desired sedation states.

23 Claims, 17 Drawing Sheets

(56) References Cited

OTHER PUBLICATIONS

Vijn and Sneyd, "I.v. Anaesthesia and EEG burst suppression in rats: bolus injections and closed-loop infusions" 1998; British Journal of Anaesthesia 81: 415-421.*

Särkelä et al., "Automatic Analysis and Monitoring of Burst Suppression in Anesthesia" 2002, Journal of Clinical Monitoring and Computing, vol. 17, No. 2, pp. 125-134.*

Lipping et al. "Adaptive segmentation of burst-suppression pattern in isoflurane and enflurane anesthesia," 1995, International Journal of Clinical Monitoring and Computing 12: 161-167.*

Beydoun, "Variance of interburst intervals in burst suppression" 1991, Electroencephalography and clinical Neurophysiology, 79: 435-439.*

"VIASYS Announces NicoletOne Modular Neurodiagnostic System; New Neurodiagnostic System Utilizes Proven EEG Technology" Business Wire, Jul. 30, 2004.

190_NicoletOne_Burst_Supression_Brochure.pdf, published after Dec. 22, 2005.

190_NicoletOne_Amplitude_Integrated_Brochure.pdf, published after Dec. 22, 2005.

NicoletOne Monitor ICU Webpage http://web.archive.org/web/20051211052422/http://www.viasyshealthcare.com/prod_serv/prodDetail.aspx?config=ps_prodDtl&prodID=188, available after Dec. 11, 2005 according to wayback. Earliest indicated date for this URL is Oct. 29, 2005.

ESCORT Vision_Central Station_Web_CP460.pdf Dec. 26, 2001 http://web.archive.org/web/20011226133537/viasyshealthcare.com/mde/Products/Central_Stations/Default.htm.

Hughes (2004) "Neurological Emergencies passage." *Neurological Emergencies*, pp. 1-492.

Leistritz et al. (1999) "New Approaches for the Detection and Analysis of Electroencephalographic Burst-Suppression Patterns in Patients Under Sedation." *Journal of Clinical Monitoring and Computing*, 15: 357-367.

Rae-Grant et al. (Type III intermittency: a nonlinear dynamic model of EEG burst suppression. *Electroencephalography and clinical neurophysiology*, 90(1): 17-23.

Schack et al. (2001) "Time-variant non-linear phase-coupling analysis of EEG burst patterns in sedated patients during electroencephalic burst suppression period." *Clinical Neurophysiology*, 112(8): 1388-1399.

Schwab et al. (2005) "Time-variant Parametric Estimation of Transient Quadratic Phase Couplings during Electroencephalographic Burst Activity." *Methods of Information in Medicine*, 44(3): 374-383.

Van Gils et al. (1997) "Signal Processing in Prolonged EEG Recordings During Intensive CareMethods for Analyzing and Displaying EEG Signals." *IEEE Engineering in Medicine and Biology*, 56-63.

EP Search Report, dated May 7, 2012 from EP Application No. 07875122.9.

* cited by examiner

| 12 SECOND BS INTERVAL |

*FIG. 4A*

| *12 SECOND BS INTERVAL* |

*FIG. 4B*

| 8.3 BURSTS PER MINUTE |

*FIG. 4C*

| *8.3 BURSTS PER MINUTE* |

*FIG. 4D*

101 | Mean BS Interval:
12 SECONDS OR 5 BURSTS PER MINUTE

102 | Confidence Value:
95%

103 | Duration of Monitoring:
1 DAY; 17 HOURS; 34.6 MINUTES

104 | Sampling Rate:
128 HZ

105 | Number Of Leads Active
FOUR

*FIG. 5*

*DOSAGE*

Titrating a drug to achieve a desired burst-suppression interval is nearly impossible as a hyperbolic dose-response curve must be coupled to distributed burst events with pinpoint accuracy.

BURST SUPPRESSION MONITOR FOR INDUCED COMA

CROSS REFERENCE TO RELATED APPLICATIONS

This application claims priority from provisional application 60/827,433 filed 29 Sep. 2006 and incorporated herein by reference.

PRECAUTIONARY REQUEST TO FILE AN INTERNATIONAL APPLICATION AND DESIGNATION OF ALL STATES

Should this document be filed electronically or in paper according to any procedure indicating an international application, Applicant hereby requests the filing of an international application and designation of all states, including the United States. Should this application be filed as a national application in the United States, this paragraph shall be disregarded.

COPYRIGHT NOTICE

Pursuant to 37 C.F.R. 1.71(e), Applicants note that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

FIELD OF THE INVENTION

The present invention relates to methods and/or systems and/or apparatuses for analysis of electroencephalogram (EEG) or related data sets and presenting clinically relevant information or taking actions based on the analysis.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

A number of patents and publications discuss various topics related to burst suppression analysis. Some of these are listed below. This list is not intended to suggest that any search has been performed and is not exhaustive. These references and their incorporated documents are incorporated herein by reference to provide background information and for any other purposes.

BACKGROUND REFERENCES

1. Principal Component Analysis and Gabortransform in analysing burst-suppression EEG under propofol anaesthesia, Laeven, R., Gielen, C. C. A. M., Coenen, A. M. L., and Van Rijn, C. M. (2001) *Sleep-wake Research in the Netherlands*, 12, 75-80.
2. Anesthesia monitoring system based on electroencephalographic signals, U.S. Pat. No. 6,317,627
3. An effective correlation dimension and burst suppression ratio of the EEG in rat. Correlation with sevoflurane induced anaesthetic depth. (2006) P. L. C. van den Broek, C. M. van Rijn, J. van Egmond, A. M. L. Coenen, L. H. D. J. Booij, *European Journal of Anaesthesiology*, May, 23 (5) 391-402.
4. Automatic analysis and monitoring of burst suppression in anesthesia. (2002), Mika Sarkela MSc, Seppo Mustola MD, Tapio Seppanen PhD, Miika Koskinen MSc, Pasi Lepola MSc, Kalervo Suominen PhD Tatu Juvonen MD PhD, HeliTolvanen-Laakso MSc and Ville Jantti MD PhD, *J Clin Monit Comput*. February, 17(2) 125-134.
5. The Narcotrend Index: Classification algorithm, correlation with propofol effect-site concentrations and comparison with spectral parameters. (2004) Schultz A, Grouven U, Berger F A, Schultz B, *Biomed Tech (Berl)*, March, 49(3) 38-42.
6. Sundt T M, Sharbrough F W, Piepgras D G, Kearns T P, Correlation of cerebral blood flow and electroencephalographic changes during carotid endarterectomy with results of surgery and hemodynamics of cerebral ischemia., Mayo Clin Proc. 1981 September; 56(9):533-43.
7. Messick J M, O'Fallon W M: Correlation of cerebral blood flow and electroencephalographic changes during carotid endarterectomy with results of surgery and hemodynamics of cerebral ischemia. Mayo Clinic proceedings 1981: 56:533-43
8. Gibbs F A, Gibbs E L, Lennox W G: Effect on the electroencephalogram of certain drugs which influence nervous activity. Arch Intern Med 1937: 60:154-66
9. J. Derbyshire, B. Rempel, A. Forbes, and E. F. Lambert (1936). The Effects of Anesthetics on Action Potentials in the Cerebral Cortex of the Cat. Am J Physiol 116: 577-596.
10. Henrey, C E, Scoville, W B. (1952). Suppression-burst activity from isolated cerebral cortex in man. Electroencephalogr Clin Neurophysiol. 4: 1-22.
11. Akrawi W P, Drummond J C, Kalkman C J, Patel P M. (1996). A comparison of the electrophysiologic characteristics of EEG burst-suppression as produced by isoflurane, thiopental, etomidate, and propofol. Journal of Neurosurgical Anesthesiology, 8: 40-6.
12. Bruhn J, Ropcke H, Rehberg B, Bouillon T, Hoeft A. (2000). Electroencephalogram approximate entropy correctly classifies the occurrence of burst suppression pattern as increasing anesthetic drug effect. Anesthesiology, 93: 981-5.
13. Leistritz L, Jager H, Schelenz C, Witte H, Putsche P, Specht M, Reinhart K. (1999). New approaches for the detection and analysis of electroencephalographic burst-suppression patterns in patients under sedation. Journal of Clinical Monitoring and Computing, 15: 357-67.
14. Lipping T, Jantti V, Yli-Hankala A, & Hartikainen K. (1995). Adaptive segmentation of burst-suppression pattern in isoflurane and enflurane anesthesia. International Journal of Clinical Monitoring and Computing, 12: 161-7.
15. Muthuswamy J, Sherman D L, Thakor N V. (1999). Higher-order spectral analysis of burst patterns in EEG. IEEE Transactions on Biomedical Engineering, 4: 92-9.
16. Sarkela M, Mustola S, Seppanen T, Koskinen M, Lepola P, Suominen K, Juvonen T, Tolvanen-Laakso H, Jantti V.

(2002). Automatic analysis and monitoring of burst suppression in anesthesia. Journal of Clinical Monitoring and Computing, 17: 125-34.

17. Bodenstein, G., Praetorius, H. M., 1977. Feature extraction from the electroencephalogram by adaptive segmentation. Proc. IEEE. 65: 642-652.

SUMMARY

In specific embodiments, the invention involves methods for monitoring and/or maintaining subjects in an induced coma state. In other embodiments, the invention involves methods for determining a burst interval in a clinically relevant setting, whether artificially induced or otherwise occurring. In other embodiments, the invention involves a system and/or method that can be used in clinical or research settings to maintain a subject at a desired state of sedation by analysis of a digital data signal representing one or more EEG signals. In further embodiments, the invention provides a device that presents a user with a measure of burst suppression that is simple to understand and does not require interpretation of EEG data.

Other Features & Benefits

The invention and various specific aspects and embodiments will be better understood with reference to the following drawings and detailed descriptions. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents. Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. All references, publications, patents, and patent applications cited herein are hereby incorporated by reference in their entirety for all purposes.

BRIEF DESCRIPTION OF THE DRAWINGS

FIG. 4A-D illustrate in simple block diagram an example display according to specific embodiments of the present invention wherein the only data displayed is a value indicating the mean interburst interval with this value displayed in black text (A) when the statistical confidence level is above a threshold and in a different text (e.g., grey, a different color, flashing, etc.) text (B) when statistical confidence level is below a designated threshold. C and D likewise show displays indicating the mean burst per minute value.

FIG. 5 illustrates an alternative example display according to the invention wherein a number of optional values in addition to mean calculation may be displayed.

DESCRIPTION OF SPECIFIC EMBODIMENTS

Figure 1:
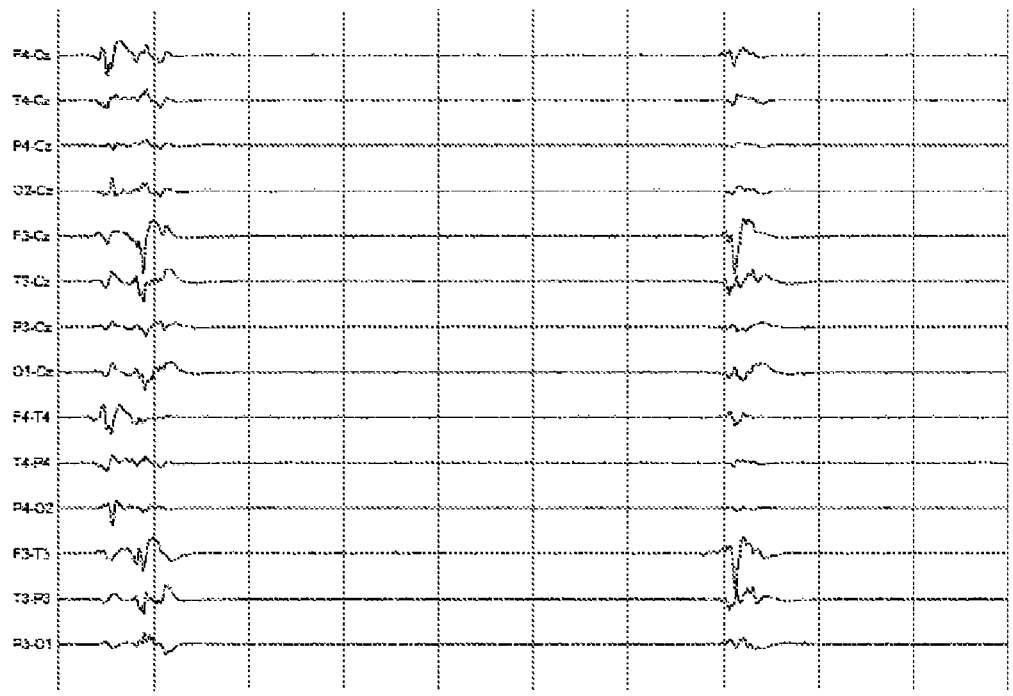
FIG. 1 is a portion of an example of EEG signal from 12 lead pairs organized by a conventional montage showing a characteristic burst suppression pattern.
Figure 2:
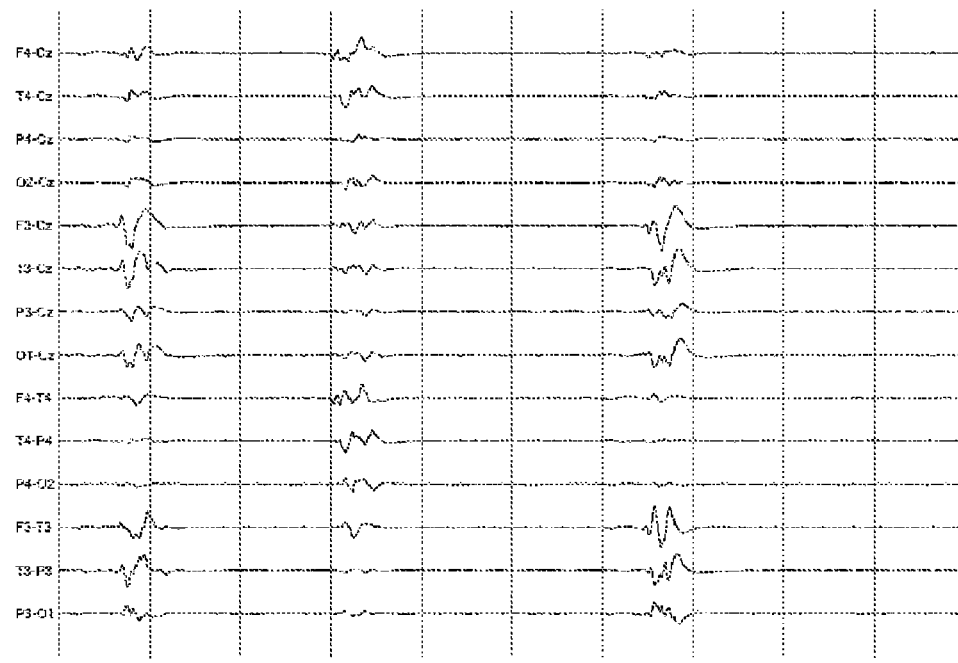
FIG. 2 is a portion of an example of EEG signal from 12 lead pairs organized by a conventional montage showing a characteristic burst suppression pattern.

Before describing the present invention in detail, it is to be understood that this invention is not limited to particular compositions or systems, which can vary. It is also to be understood that the terminology used herein is for the purpose of describing particular embodiments only, and is not intended to be limiting. As used in this specification and the appended claims, the singular forms "a", "an" and "the" include plural referents unless the content and context clearly dictates otherwise. Thus, for example, reference to "a device" includes a combination of two or more such devices, and the like.

1. Overview

Burst-suppression (BS) is an electroencephalographic (EEG) pattern typically described in the relevant literature as characterized by alternating segments of high amplitude burst followed by relative suppression of EEG activity. This pattern is observed in a number of clinical or research situations and is observed in human as well as in animal subjects.

Much research has focused on using an EEG in the study the pharmacodynamic effects of anesthetic drugs. EEG technology has also fostered the development of at least one important pharmacologic intervention: benign neuropharmacologically-induced burst-suppression. This type of Burst Suppression is currently utilized in the treatment of such conditions as highintracranial pressure (ICP) and status epilepticus.

A dilemma has emerged with the use of EEG technology in such neurotherapeutic contexts: EEG allows sensitive, accurate, and constant monitoring of a patient's electrophysiology and depth of consciousness (Rampil, 1998), which is significant, but the amount of information generally provided makes it difficult for human review, particularly in clinical settings, such as a hospital. Automated computerized analysis of EEG has been a long felt need of neuroscientists and physicians. This problem is especially serious for EEG Burst-Suppression treatment where a patient may be monitored for days at a time and where improper levels of sedation may hinder recovery.

EEG burst suppression (BS) was first observed in animals and much current understanding comes from an animal model (Akrawi et al., 1996). In humans, non-induced BS is associated with epileptic encephalopathy in infancy or childhood, severe anoxia, and rare cerebral tumors which undercut the cortex and produce regional BS.

The International Federation of Societies for Electroencephalography and Clinical Neurophysiology (IFSECN) defines burst suppression as a "pattern characterized by theta and/or delta waves at times intermixed with faster waves, and intervening periods of relative quiescence" (Chatrian et al., 1974). However, this definition fails to capture the nature of neuropharmacologically-induced BS clearly. Neuropharmacologically-induced BS is generally characterized as primarily consisting of spikes or grouped spikes with usually one spike of immense amplitude.

Niedermeyer et al. (1999) provides criteria for classifying the presence of induced BS based on duration and amplitude of burst, suppression, and their ratio. These criteria, while possibly somewhat imprecisely selected, are quantitative and they also dictate further exclusion of BS occurring at any age during sleep to distinguish it from activity observed in prenatal sleep as well as the sleep of children with hypsarrhythmia. BS is an intermediate state during recovery from anoxia-induced isoelectricity, a modification of anoxic cerebral pathology presumably associated with modern intensive care. BS was relatively unknown in thorough investigations of anoxia of last century. As a simplification, an EEG signal during burst-suppression coma can be understood to consist of bursts, suppressions, and occasional artifact.

In one clinical application of monitored induced coma or burst suppression sedation, patients with convulsive status epilepticus or with high intracranial pressure (ICP) are often put into an induced BS coma by administering hypnotics or other anesthetics in order to achieve sufficient sedation to help resolve a clinical problem. The depth of anesthesia is often assessed by monitoring an interburst interval on an EEG trace, although other EEG parameters have also proven to be of clinical value including BS rate and dominant frequency of the burst.

In long term ICU monitoring, visual differentiation between burst periods and suppression periods is performed usually by nursing staff who attempt to calculate an interburst interval, for example from the EEG timeline, and titrate hypnotics based on the calculated interval. This process, however, is error prone and burdensome to the staff and can result in over- or under-sedation of the patient. Typically, in this process, nursing staff attempt to visually estimate one or a few interburst intervals and then must watch for sometimes subtle changes in that interval in response to adjustments in the titration.

A common problem in burst or suppression detection is in localizing the exact onset of either event. The common use of fixed interval segmentation of the EEG with no or insufficient overlap of segments exacerbates the problem (e.g., Thomsen, 1992; Sarkela et al., 2002; Lipping et al., 1995). Another problem in typical BS analysis is a fundamental mischaracterization of the phenomenon in terms of detection. According to specific embodiments of the invention, EEG bursts are best characterized as rapid voltage change followed by modest voltage change (i.e., suppression) instead of activity and inactivity cycles. Conceiving bursts as states of high amplitude instead of states of high variability have led some researchers to analyze absolute amplitude instead of amplitude differences. Similarly, the use of Fourier analysis is common, but this approach involves prerequisites that may be unsuited for accurate timing of burst-suppression boundaries.

In many prior art approaches, attempts to distinguish bursts from suppression, with varying degrees of success, were performed through linear or non-linear means, with the most common approach relying on spectral analysis. Akrawi et al (1996) compared low and high frequency power in rats to identify bursts. Muthuswamy et al (1999) utilized bicoherence analysis, a form of spectral analysis that examines stationary of phase differences within a single signal across frequencies. A classification scheme independent of the agent used to induce the coma is obviously preferred, but these attempts determined that isoflurane, thiopental, etomidate, and propofol all differ significantly from each other, except etomidate from propofol, in burst duration, maximum peak-to-peak voltage, and area under the curve (Akrawi et al., 1996). Most techniques use a single bipolar site-pair for measuring the EEG signal, often frontal pole to central strip (e.g., Sarkela et al., 2002; Bruhn et al., 2000; Leistritz et al., 1999), as well as sliding data windows. The rate of slide, also called window saturation, directly limits the accuracy of any classification scheme. Sarkela et al (2002) utilized 1 second data windows that slid 100 ms, which results in a boundary detection error of +/−50 ms. Researchers who use only tiled windows (minimal contiguous saturation) are further disadvantaged (e.g., Bruhn et al., 2000).

As a further example, the BSR (burst suppression rate) detector in the Bispectral Index (BIS) monitor, the most well known BS detection system, appears to rely on a time domain threshold detection scheme smoothed for 60 seconds and bolstered by a slow wave filter (<1 Hz) in order to identify bursts (Rampil, 1998). Sarkela et al. (2002) developed an automatic segmentation and classification technique based on EEG spectral characteristics with an error rate of 7%, comparable to the sensitivity and specificity of Liestritz et al. (1999). Lipping et al. (1995) reported a 2% error rate but their data contained very little artifact and was poor in detecting actual artifact, making it impractical as a real-world application.

In specific embodiments, the present invention utilizes a novel characterization of burst-suppression activity as one of voltage variability rather than primarily voltage amplitude. Methodological considerations also improve boundary detection (i.e., burst offset, burst onset) by avoiding spectral analysis and utilizing time-domain analysis with maximal window saturation. In developing the invention, it has been found that reliance on anything but maximal window saturation (e.g., a data window begun at every digitized sample) increases error unnecessarily, proportionally to the size of the window. In specific embodiments of the invention, artifacts management can also be improved by relying on multiple electrode positions using common mode rejection of electrical artifacts.

2. Computer-Aided Burst Detection Algorithm

The present invention involves an automatic computer-aided burst detection algorithm to relieve hospital or other staff of the task of estimating burst suppression intervals and to improve patient care by providing information enabling more appropriate titration of sedatives. In specific embodiments, a method or system of the invention provides a display of a more accurate interburst interval mean along with statistical confidence of this mean.

According to specific embodiments of the invention, computation of the burst suppression interval (also referred to as interburst interval) in an ongoing EEG involves identification of burst from suppression. Such identification is attained by timing the presence of bursts in an otherwise isoelectric or noisy signal and subjecting this sample to statistical analysis. According to specific embodiments of the invention, burst onset is identified by computing changes in amplitude at every data sample point with appropriate smoothing and proper threshold differentiation.

Automatic identification and characterization of burst-suppression activity according to specific embodiments of the invention in ongoing EEG has many clinical applications including its use in titrating hypnotics in order to reach an appropriate stage of sedation. While some prior automatic classification schemes provide fair accuracy, they generally are not accurate enough to be incorporated into an automatic closed-loop titration of an anesthetic or to provide optimum guidance to a human administering an anesthetic. Classification algorithms generally differ from manual identification 5 to 10% of the time, a failure rate due to methodological as well as conceptual considerations.

According to specific embodiments of the invention, the invention provides an algorithm, a specific example of which is described below, that provides, with statistical confidence, a mean BS (or interburst) interval practically for any desired point in time. BS interval according to specific embodiments of the invention is defined as the time between burst offset and subsequent burst onset, regardless of burst duration.

According to further specific embodiments, the algorithm calculates and displays with statistical accuracy the mean BS interval in patients placed into induced coma. In typical current practice, this interval is not calculated at all and a guess or visual estimate of one or a few interburst intervals is made.

Prior to this invention there have been several algorithms and devices displaying the trending. Some devices provide graphical information about the interval, without statistical confidence, which excludes the practical application of sedation titration based on this but generally, these devices did not actually present to staff the statistically true interval so staff could titrate appropriately.

Figure 3:
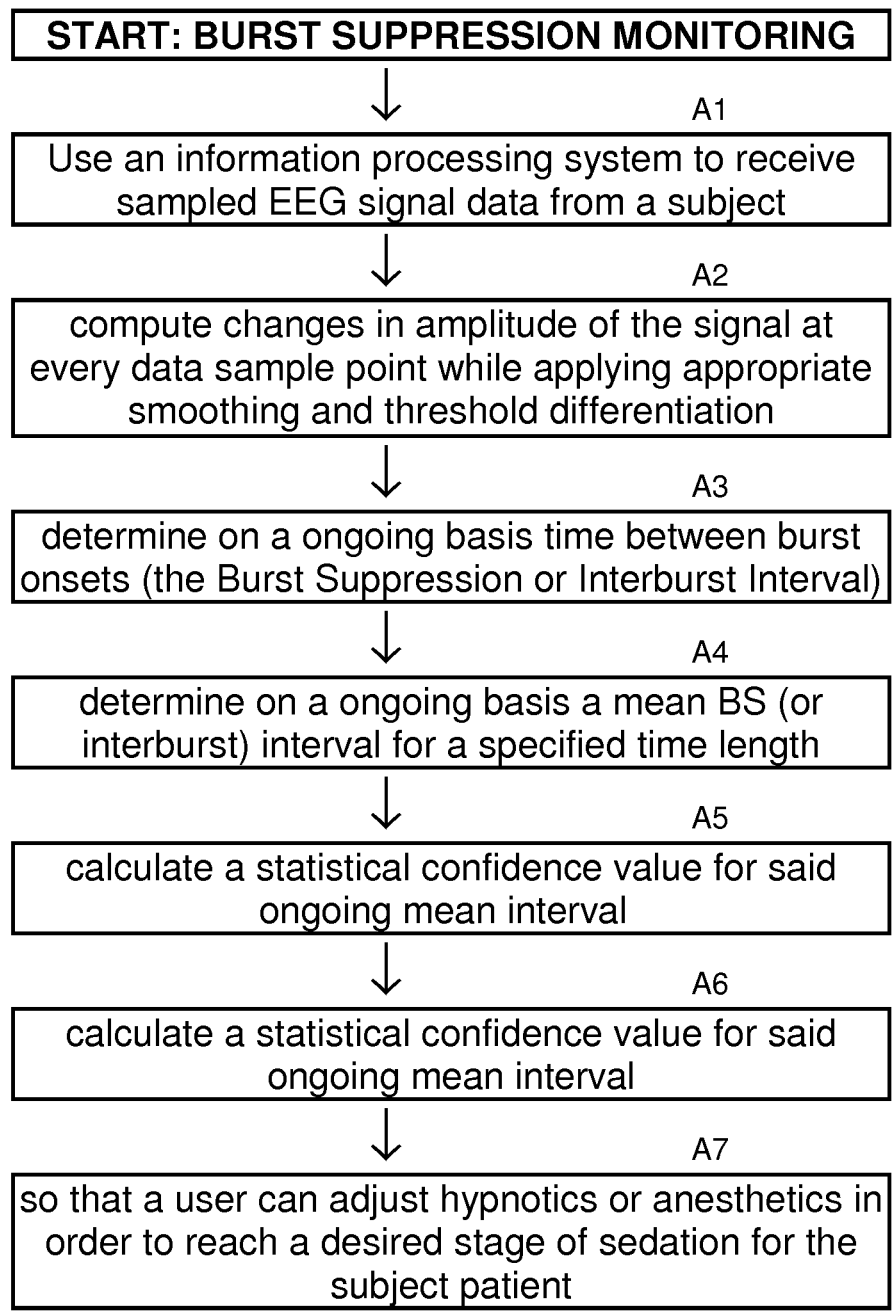
FIG. 3 is a flow chart illustrating a method of adjusting a patient's or subject's sedation according to specific embodiments of the invention.
Figure 6A:
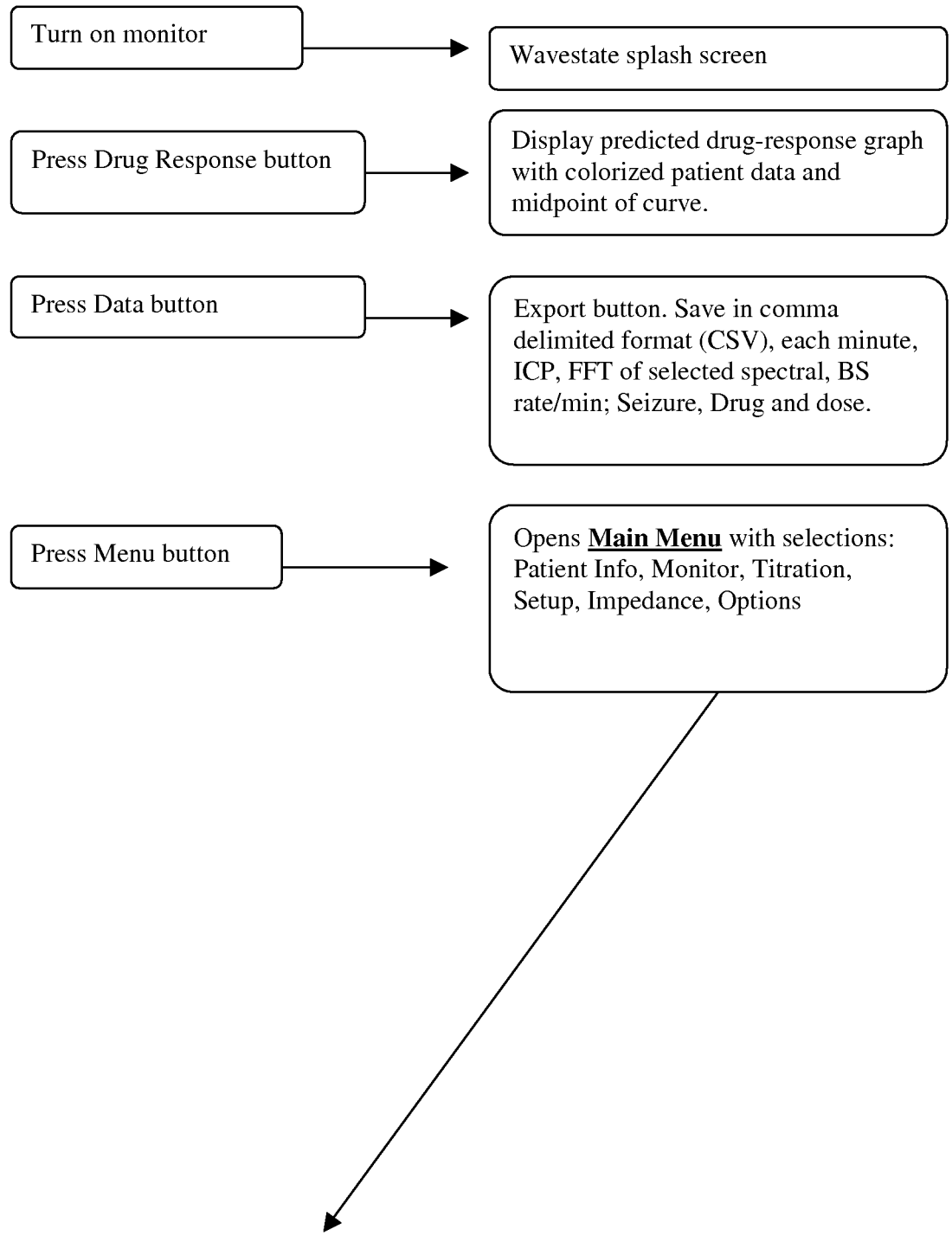
FIG. 6A-D provide an example flow chart of a user interface operation according to specific embodiments of the invention.
Figure 6B:
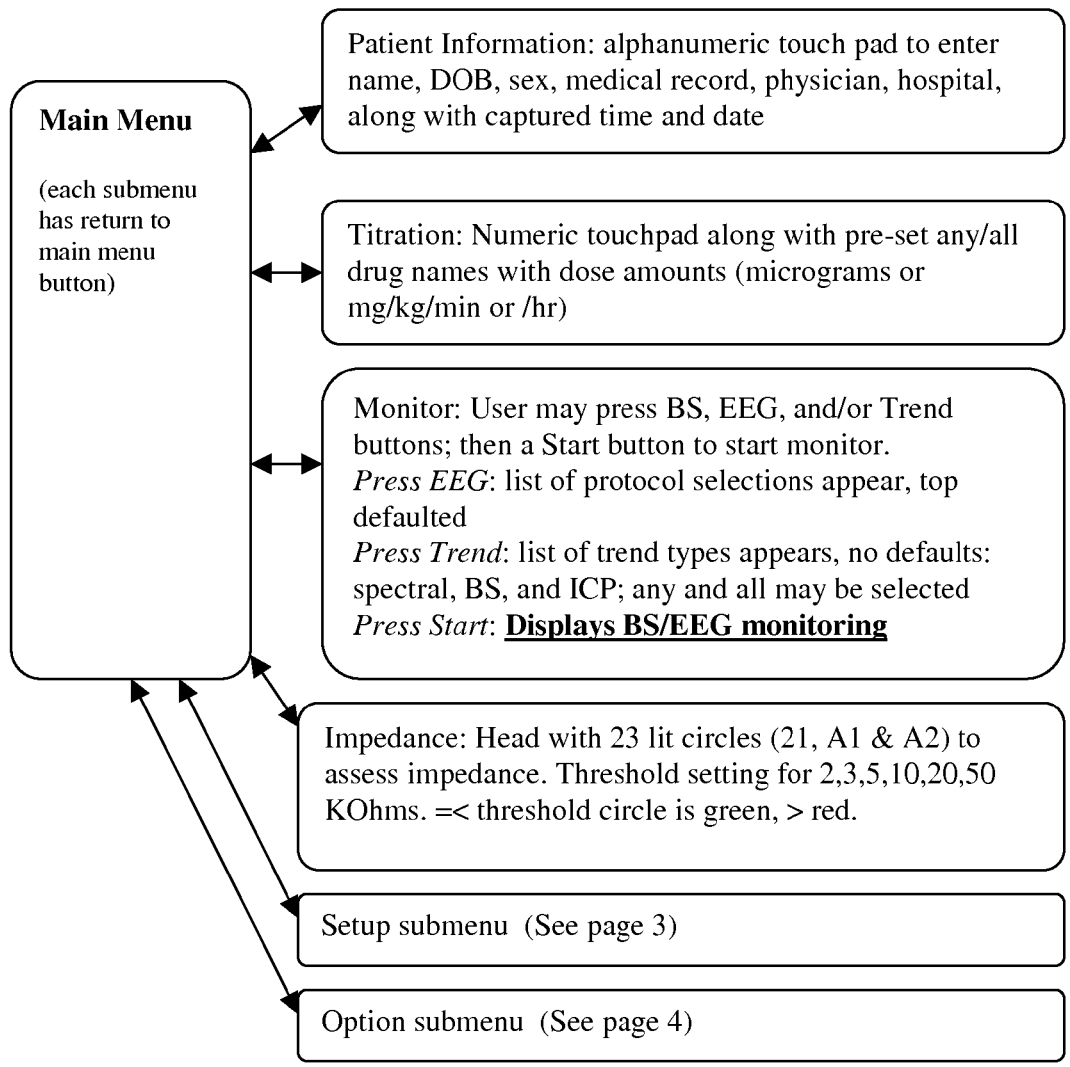
Figure 6C:
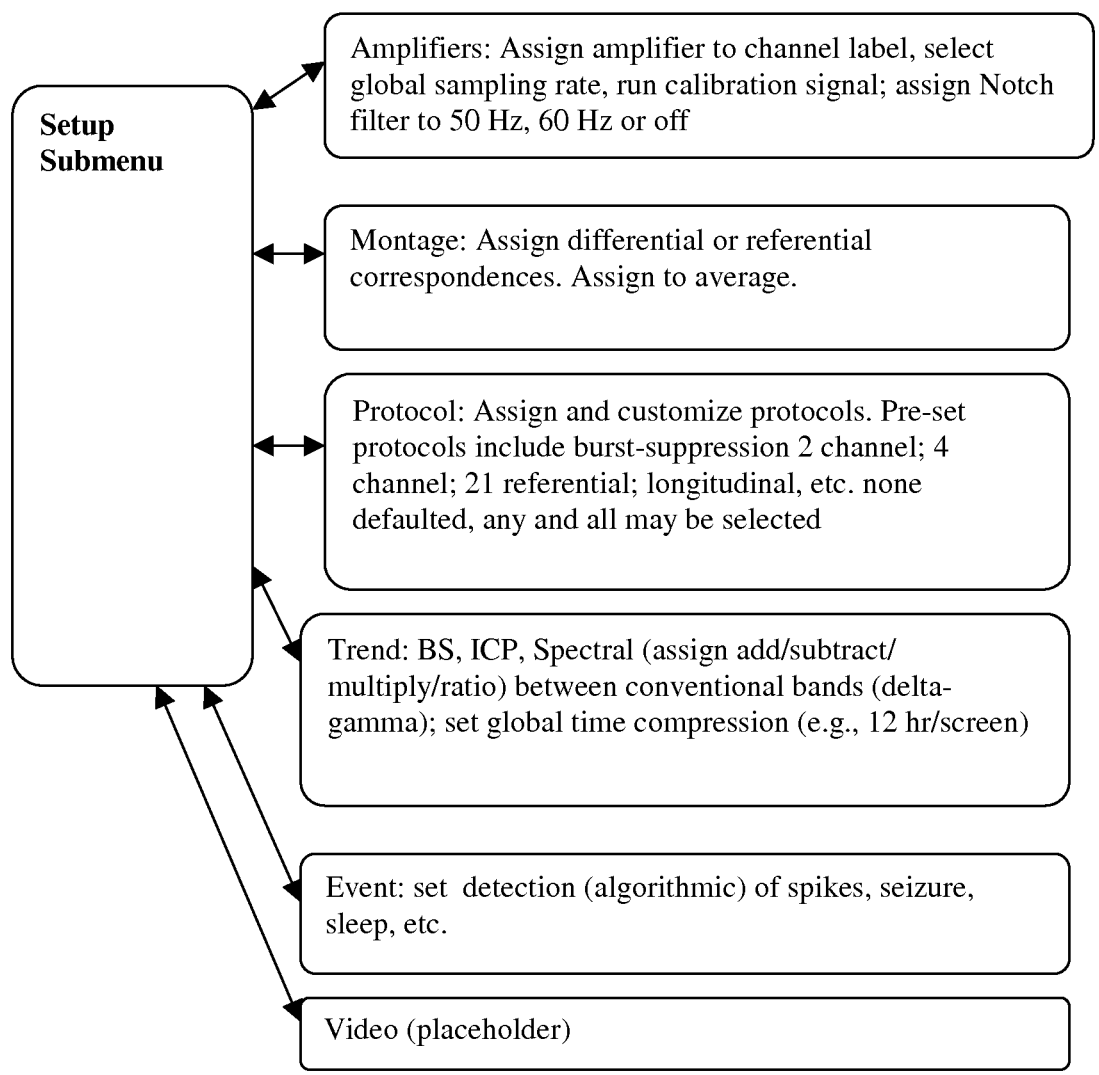
Figure 6D:
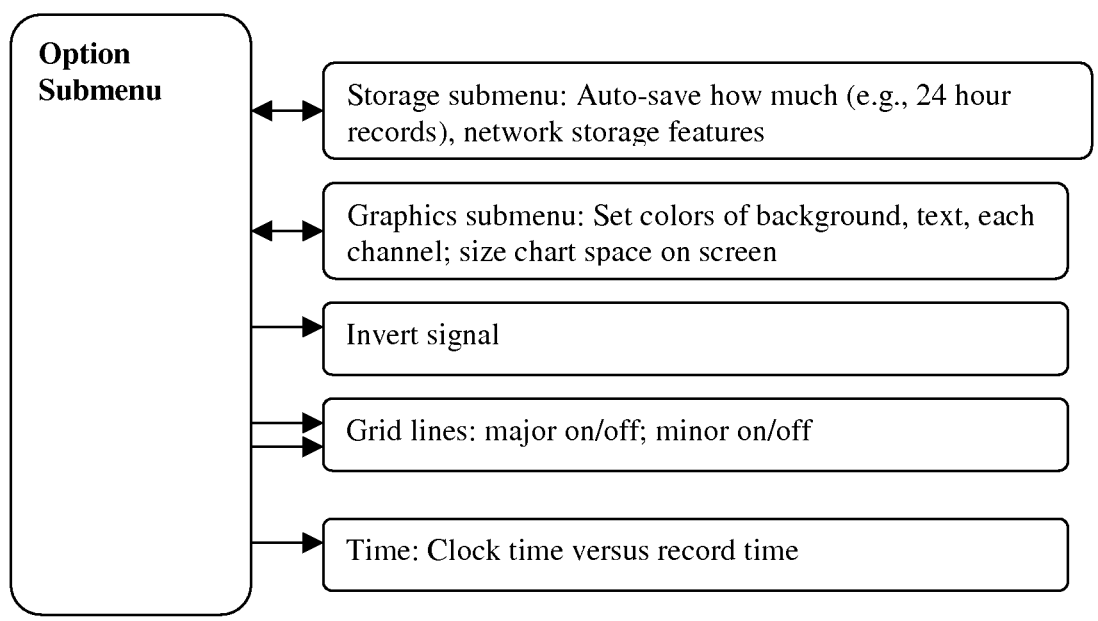
Figure 7A:
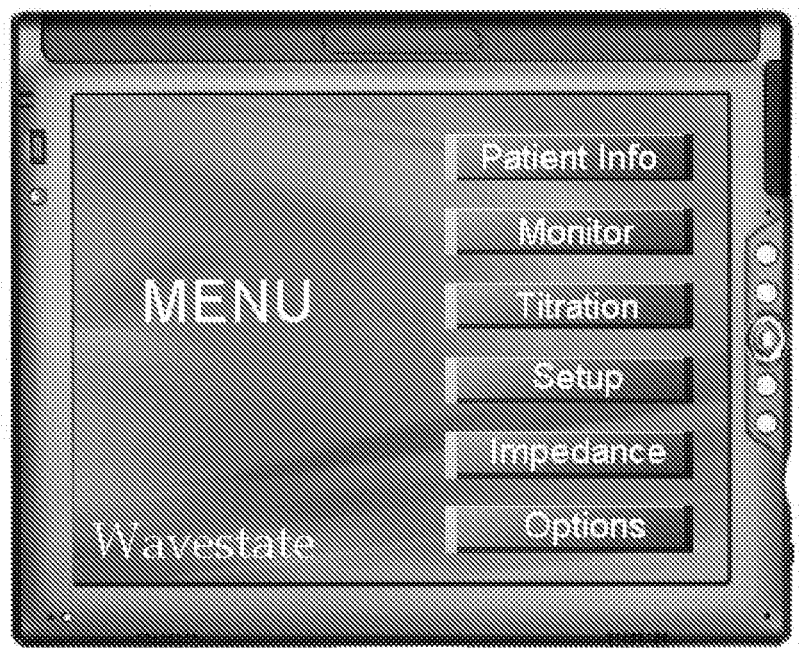
FIG. 7A-G illustrate example graphical user interfaces showing an initial menu screen and other user data input screens as may be displayed on special purpose or general purpose persona computers, tablet computers, or information laboratory equipment according to specific embodiments of the invention.
Figure 7B:
Figure 7C:
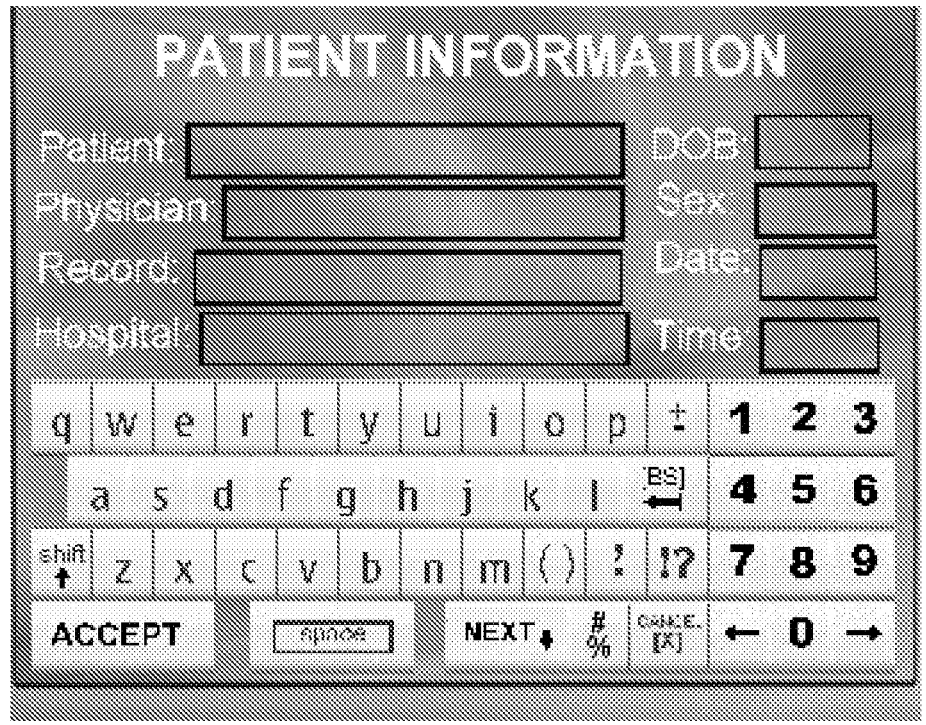
Figure 7D:
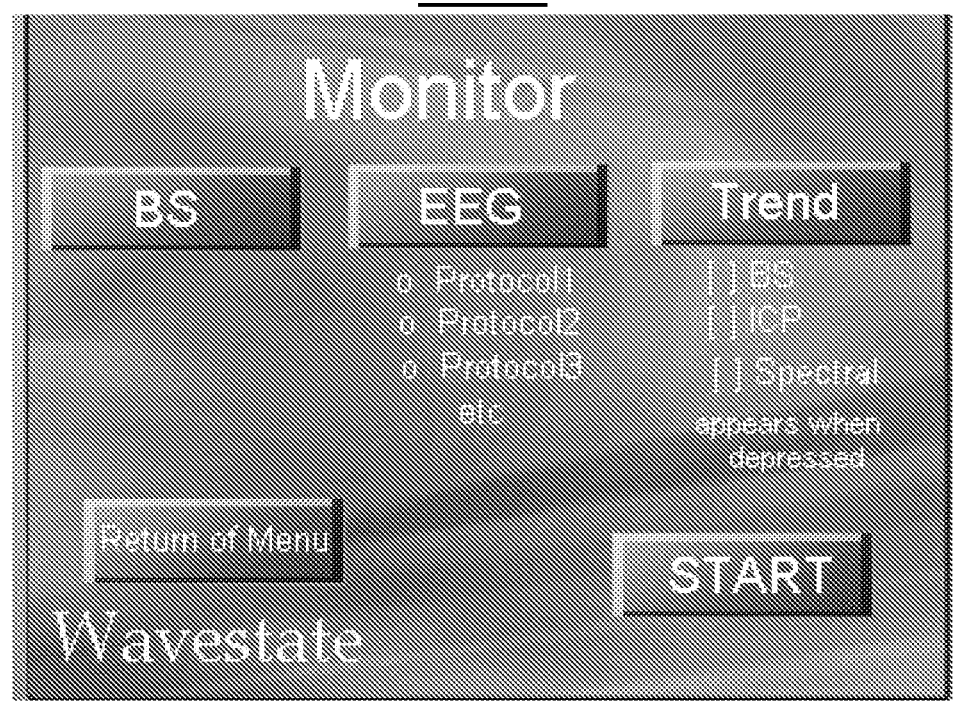
Figure 7E:
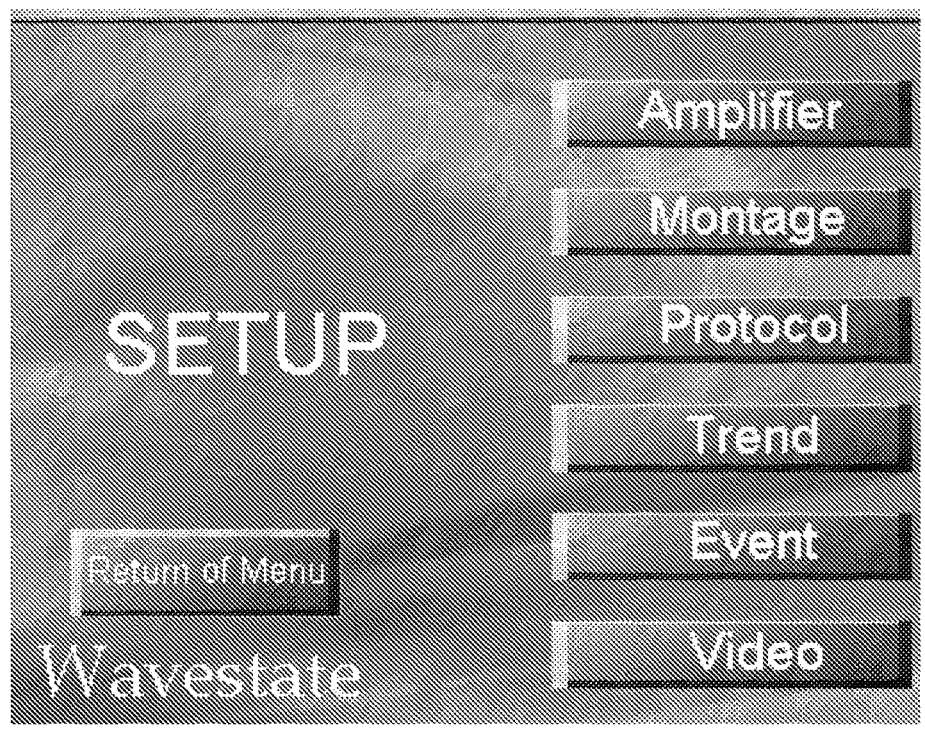
Figure 7F:
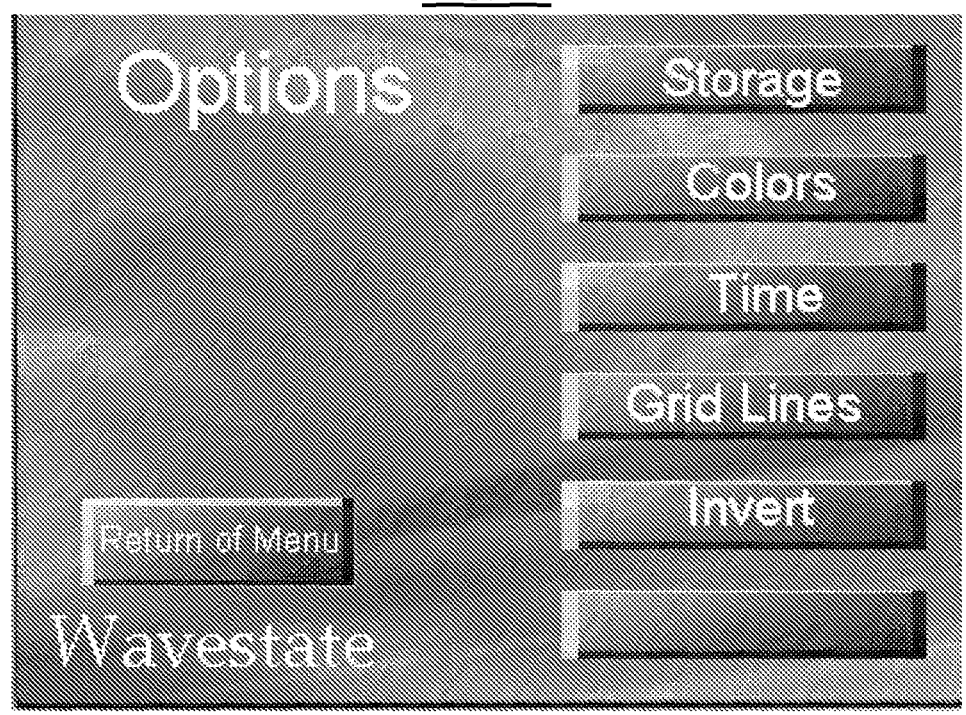
Figure 7G:
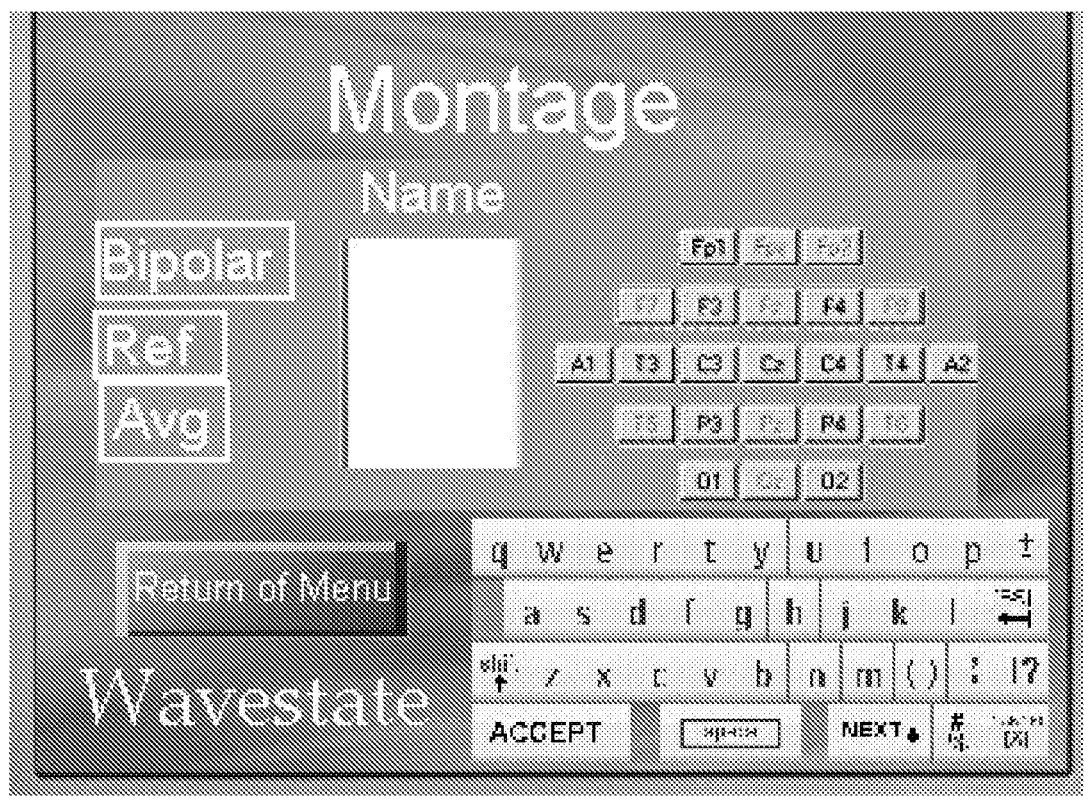

FIG. 3 is a flow chart illustrating a method of adjusting a patient's or subject's sedation according to specific embodiments of the invention. This figure illustrates a general embodiment. In an example method, EEG signal data is received (Step A1), changes in amplitude are determined (Step A2) and an ongoing interburst interval is calculated (Step A3). As the signal continues to be received, an ongoing mean of the interburst interval is computed (Step A4) and a statistical confidence value is computed (Step A5). The medical staff user is presented with the computed ongoing mean along with an indication of confidence (Step A6) and uses that information to adjust application of sedatives or hypnotics (Step A7).

As will be further understood from the teachings provided herein, the present invention encompasses a variety of specific embodiments for performing these steps. In various embodiments, indications of burst suppression calculations can be presented to a staff member using a graphical or numeric or textual interface and/or using various audio indications.

3. Other Characteristics

In prior approaches that use EEG segmentation, where EEG is segmented into fixed intervals (e.g., 1 second data windows) with no or insufficient overlap, it is generally not possible to localize the exact onset of a burst or suppression. Data windows generally smear onset detection as a function equal to the rate of overlap or the segmentation interval (when tiling/no overlap is used).

The present invention avoids this problem by not segmenting the EEG signal EEG signals but instead analyzing each and every digitized EEG sample for a burst or suppression onset. Thus, the invention achieves instantaneous detection, which has proven far superior to windowed detection.

Burst-suppression has also been conceptualized poorly in prior algorithm detection literature as a state of EEG silence followed by a state of discharge. This description misses the aspect of the signal that is most indicative of the difference between bursts and suppression. While EEG silence is a state of modest voltages, it more importantly is a state of modest voltage change, whereas a burst is a state of large voltages, but more importantly it is a state of large voltage change. This difference is subtle but critical in identifying exact burst or suppression onset or offset. Other algorithms that use temporal detection schemes look for differences in voltages across time. In the present invention, the detection algorithm identifies voltage differences in real time. In other words, the invention uses the constant change in positivity to negativity to advantage in its detection scheme whereas absolute voltage detection schemes smear across such chatter.

In specific embodiments, the interval calculation and display is a statistical event with a confidence interval of e.g., 95%. That is, an assumption employed by the invention is that at any dose of hypnotic, the brain will be bursting around a statistical mean or median. By reporting and/or utilizing this estimate of the phenomenon's central tendency, the invention allows for stabilizing titration or other administration of an anesthetic agent. In other schemes, if an ongoing average without statistical confidence is reported the patient may be subject to under- and over-dosing based on the sample's average interval as the true (population) interburst interval is not known.

According to specific embodiments, the invention is embodied in a single application (e.g., only burst-suppression) device that is portable hardware and for example that may involve two or more leads attached to the head of the patient. Further, no expertise in EEG is required as the only display will be interburst interval in a format understood by staff, although in alternative embodiments, full EEG charting is possible but not necessary.

4. Further Details of an Example Method According to Specific Embodiments of the Invention Pre-Processing Pre-processing of an EEG signal to minimize noise is normally achieved by application of a low-pass digital filter or mathematical smoothing and this can be performed before a signal is outputted from the EEG recording device. Also, a high pass digital filter of 3 Hz may be applied to remove slow drifts due to poor electrode contact, sweat, slow cortical potentials, or related artifact. Finally, physiological and equipment artifact may be minimized by numerous artifact detection schemes, including elimination from further computation any short segment of EEG (e.g., 100 ms) with an absolute amplitude average of 100 microvolts or above. According to specific embodiments of the invention, further noise reduction is achieved by appropriate amplitude comparisons as described below. Furthermore, computations are for the most part performed for every digitized sample with ongoing updating of histories as described in further detailed examples below.

As an example, in a 128 samples per second signal, a 3-sample-skip comparison provides noise reduction comparable to a 4-sample smooth or 32 Hz low pass filter. A 3-sample skip requires that amplitude at time 0 is compared to amplitude at time 3, amplitude at time 1 to amplitude at time 4, and so on, consecutively across the signal. A 1-sample skip may also be used to capture rare low-amplitude bursts in some patients, though interval estimation should not change appreciably and in specific embodiments, a 2-sample skip is used.

According to alternative embodiments of the invention, data from multiple EEG channels may be used to detect variance in BS generation across scalp recordings, which in some situations may strengthen the reliability of the detection scheme. However, in some implementations, a single EEG channel or bipolar pairing can be used for analysis, preferably one with the greatest measured amplitudes. Anterior or lateral sites referenced to vertex such as F3-Cz or T3-Cz work well. In a typical clinical implementation, generally at least two and typically four channels are analyzed.

Computing Voltage Amplitude Difference

In specific embodiments, absolute amplitude difference ($d_i$) in microvolts is calculated continuously across the signal, with a 1 second history (i.e., smoothed 1000 ms). Smoothing minimizes the effect of signal variation on onset detection. modest history (e.g., 500 to 1000 ms smoothed). The invention can be further understood by considering the equation:

$$d_i = \frac{1}{R}\sum_{i=1}^{R}[A_i - A_{i-4}],$$

where A=amplitude of sample i, R=sample rate/sec, which typically is about 128 samples/sec. In one example embodiment, 4 was selected as best smoothing/skip parameter for the 128 sampling rate. However, this number can be adjusted in various applications. In this equation, both the sample skip difference and the smoothed 1 second summation over the previous R samples are indicated.

According to specific embodiments of the invention, burst onset is detected when the smoothed absolute amplitude difference ($d_i$) exceeds a criterion based on median (m) absolute amplitude times a specified factor. The multiplication factor is the cube root of burst-suppression duration ratio, with extreme values truncated (e.g., values above 2 reduced to 2). For instance, an interval with 5:1 burst-suppression duration ratio has 1.71 as its multiplication factor, so that detection occurs at 1.71 times median. This factor is be defaulted to an appropriate goal interburst interval (e.g., 1.5 seconds) at the start of computation.

Suppression onset occurs whenever the smoothed absolute amplitude difference ($d_i$) drops below 1× median (m) absolute amplitude. The median absolute amplitude is calculated for a long running history consisting of at least two interburst intervals. Initial median absolute amplitude is computed for 10 seconds and may be updated periodically, e.g., every 30 or 60 seconds, until multiple interburst intervals have been detected. Median computation occurs at each burst offset (i.e., start of suppression). Median absolute amplitude is mean median and computed in such a way as to be moderately intolerant of outliers, i.e., significant deviations from past median values on the part are eliminated and current or past intervals are eliminated and/or weighted accordingly. For instance, if the current interval's median is more than 2 standard deviations away from the mean of the median distribution, it does not contribute to the mean median and if the current median is within 2 standard deviations of the mean median, it contributes to the mean median. The median-based criterion is made more sensitive to the current moment by weighing all contributions to the mean median based on temporal distance from current moment using either a linear, exponential, or logarithmic decay function. For instance, to compute the representative median for the current interval using exponential decay, each median contributes twice the weight of the previous median.

In experimental work, 2× median was chosen empirically as the threshold value to determine burst onset. However, this value can be adjusted in various embodiments or situations, including utilizing a per patient analysis. In specific embodiments, the value is learned by an algorithm that analyzes either initial data or training data.

In further examples, this can be understood as involving $P(|A|\leq m)=P(|A|\geq m)=\int_{\infty}^{m}f(|a|)d_a=0.5$, where P=probability.

In various embodiments, P determines how the BSMBS interval is presented to a staff member or used. For example the BSM can be displayed in different colors based on the value of P, or the BSMBS interval can flash or blink until P rises above a predetermined value. In this way, medical staff can determine whether the BSMBS interval displayed is the "true" value or a value accurate (statistically speaking), with sufficient statistical confidence and can thereby more accurately make any necessary adjustments to perform a necessary adjustment of the anesthetics.

In some embodiments, an additional smoothing factor may be applied to minimize the detection of rapid consecutive burst onsets. Suppression onset is ignored whenever a burst onset occurs less than 500 or 1000 ms after the suppression onset. This smoothing factor is optional and generally unnecessary for modestly-delineated delineated BS.

In specific embodiments, burst onsets are tallied and presented after a period of time (e.g., the first minute) in units of Bursts per Minute. In specific embodiments, a history of this measure can also be set by the user, e.g., to 5 minutes throughout the recording or longer (e.g., 10 minutes, 30 minutes) or if empirically derived depending upon a designated state of statistical confidence desired by a user.

In some embodiments, time count (e.g., number of digitized samples (e.g., typically such as 128 samples per second) since last burst onset) is be reset to zero at each burst onset. In this situation, time count immediately prior to reset can be used to compute current BS interval.

Mean Burst Suppression Interval

In specific embodiments of the invention, Mean Burst Suppression Interval ($\bar{b}/R$) is displayed in units of seconds (e.g., 8.5), along with a statistical confidence of this estimate for the unit range. Generally, the time count of the first burst onset of any record is ignored.

$$\bar{b} = \frac{1}{n-1} \sum_{j=2}^{n} b_i$$

n=number of intervals collected
j=tally or count or array of number of intervals collected
$t_i=t_i+1$
t=time count since last burst.

According to specific embodiments of the invention, b refers to number of digitized samples from burst offset to burst onset and R equals sample rate. Number of digitized samples may be represented linearly, logarithmically, or exponentially. In the equations below, c is a variable indicating a classification of state as either burst or suppression.

if $d_i/2 > m_i$, $c_i=1$, if $d_i < m_i$, $c_i=0$.

else $c_i=c_{i-1}$ if $c_i=c_{i-1}+1$ then if $t_{i-1}<R$, $c_i=c_{i-1}$ if $t_{i-1} \geq R$, $b_j=b_{j+1}$, $b_j=t_{i-1}$, $t_i=0$ In further embodiments, confidence is indicated at 95% if $$\frac{s}{\sqrt{n}} > .166R$$

for 1 minute for a designated degree, such as 95% if $$\frac{s}{\sqrt{n}} > .166R$$

given the standard deviation of burst intervals and number of intervals, see below. This produces a confidence interval of approximately 1 second around $\bar{b}/R$, assuming a unimodal symmetric distribution of interval data in accordance with Tchebycheff's inequality. Larger confidence intervals (e.g., ±2 seconds) may also be computed readily as well.

$$s = \sqrt{\frac{1}{n-1} \sum_{j=2}^{n} (b_j - \bar{b})^2},$$

where s=standard deviation; n=number of intervals

In specific embodiments, the algorithm characterizes burst-suppression intervals with statistical confidence and with minimal conceptual or procedural complexity. The possibility of burst or suppression onset, offset, and duration are determined for each and every digital sample. Smoothing and threshold factors are empirically validated in specific embodiments for a large patient sample. Adjustments may be made to increase or decrease specificity or selectivity for specific cases or populations.

5. Presentation to Users

FIG. 4A-D illustrate in simple block diagram an example display according to specific embodiments of the present invention wherein the only data displayed is a value indicating the mean interburst interval with this value displayed in black text (A) when the statistical confidence level is above a threshold and in a different text (e.g., grey, a different color, flashing, etc.) text (B) when statistical confidence level is below a designated threshold. C and D likewise show displays indicating the mean burst per minute value. As described above, such displays are particularly useful to staff in a patient care setting as the display succinctly and accurately provides staff with the essential information needed to monitor burst suppression activity. Alternate example displays discussed herein provide further functionality.

FIG. 5 illustrates an alternative example display according to the invention wherein a number of optional values in addition to mean calculation may be displayed. Different levels of detail can be displayed according to specific embodiments of the invention and in some embodiments a monitoring system of the invention may provide options allowing a user to select which portions of data are displayed.

FIG. 6A-D provide an example flow chart of a user interface operation according to specific embodiments of the invention. This chart is provided for illustrative purposes only and it will be apparent to those of skill in the art that other user interactions steps may be used to effect the present invention.

FIG. 7A-G illustrate example graphical user interfaces showing an initial menu screen and other user data input screens as may be displayed on special purpose or general purpose persona computers, tablet computers, or information laboratory equipment according to specific embodiments of the invention. A number of different screens are optionally included according to specific embodiments of the invention for various user interface tasks such as patient information management and other data and file information management.

Figure 8:
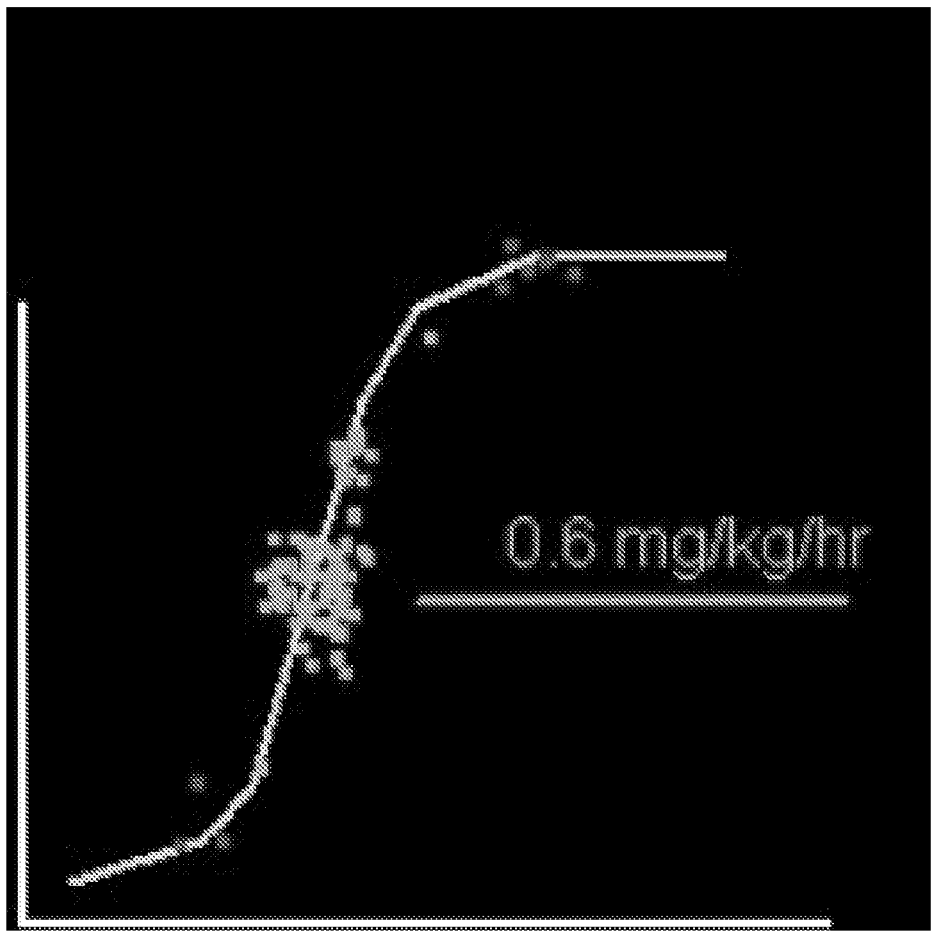
FIG. 8 illustrates an example graphical user interface showing a novel display generated as a single curve from a monitoring of a live subject plotting a dosage of a anesthetic agent on the horizontal axis and a response in terms of an inter-burst interval or the vertical axis according to specific embodiments of the invention with individual points clustered at the center (and indicated in green, for example) indicating appropriate suppression and outlining points (for example colored red) at the top and bottom of the graph indicating over or under sedation.
Figure 9:
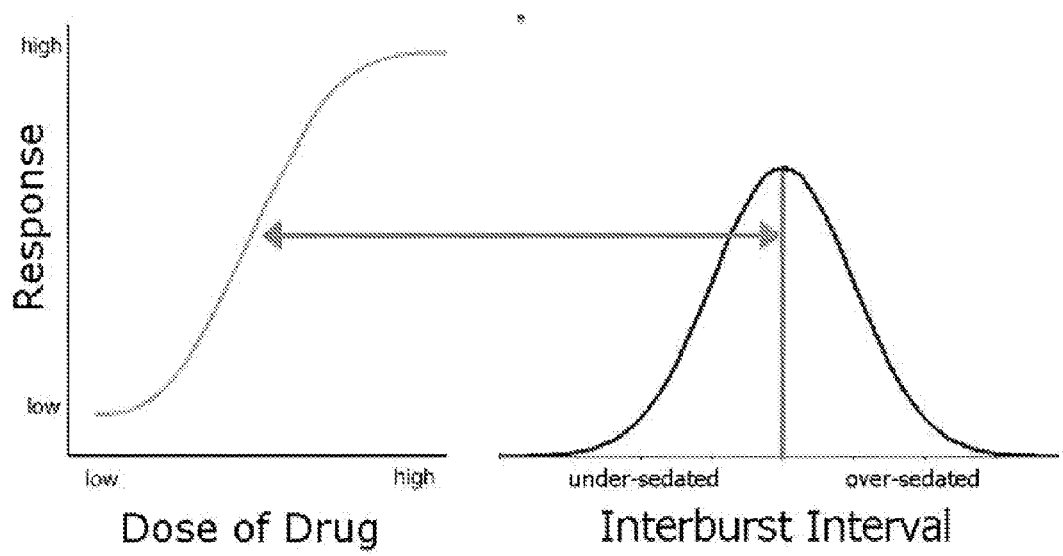
FIG. 9 illustrates as an example illustrating that using a computer to monitor burst interval according to specific embodiments of the invention is advantageous: to the right is shown an example dose/response curve which, as is typically the case, indicates that near the desired dose range, the response varies widely depending on the dose; to the right is show a peak curve with a steep fall-off on either side indicating that the desired interburst interval (e.g., about 10 seconds) is quickly deviated from when the dosage changes from optimum. Thus, the present invention provides a more effective means for managing the dose/response relationship.

FIG. 8 illustrates an example graphical user interface showing a novel display generated as a single curve from a monitoring of a live subject plotting a dosage of a anesthetic agent on the horizontal axis and a response in terms of an inter-burst interval on the vertical axis according to specific embodiments of the invention with individual points clustered at the center (and indicated in green, for example) indicating appropriate suppression and outlining points (for example colored red) at the top and bottom of the graph indicating over or under sedation. This display provides information allowing a staff person to either administer and monitor titration of sedatives and burst suppression according to specific embodiments of the invention or this display represents data that can be used for automatic titration according to specific embodiments of the invention. In this figure, green dots indicate a patient time sample where the sedation is correct.

Figure 10:
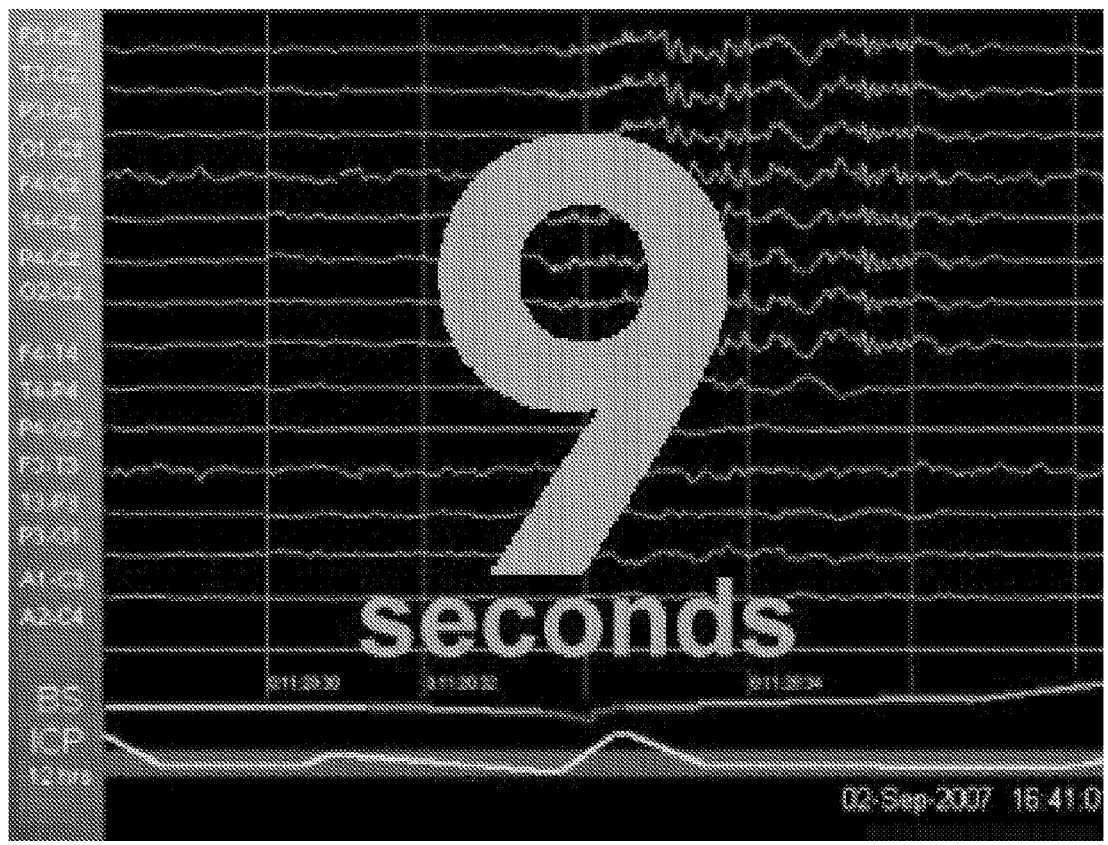
FIG. 10 illustrates an example graphical user display according to specific embodiments of the present invention wherein the most prominent data displayed is a value indicating the mean interburst interval, for example in a color or with flashing indicating if a desired confidence interval has been achieved; optional additional data according to various embodiments of the invention include an BS history graph (in this case for 12 previous hours) showing an initial period when not enough data has been gathered to determine a BI with the desired confidence, a green indication then the BI is in the desired range and is calculated with the desired confidence, a red jagged period near the center of the graph indicating a period when the confidence interval falls out of a desired threshold; an ICP history is also provided, along with a bar indicating a range of target ICP and wherein exceeding the targeted ICP corresponds to the exceeding of confidence for the BI calculation.

FIG. 10 illustrates an example graphical user display according to specific embodiments of the present invention wherein the most prominent data displayed is a value indicating the mean interburst interval, for example in a color or with flashing indicating if a desired confidence interval has been achieved; optional additional data according to various embodiments of the invention include an BS history graph (in this case for 12 previous hours) showing an initial period when not enough data has been gathered to determine a BI with the desired confidence, a green indication then the BI is in the desired range and is calculated with the desired confidence, a red jagged period near the center of the graph indicating a period when the confidence interval falls out of a desired threshold; an ICP history is also provided, along with a bar indicating a range of target ICP and wherein exceeding the targeted ICP corresponds to the exceeding of confidence for the BI calculation.

In this example figure, the BS trace is a trending history of the BSI in time. That time is selectable by a user, such as 4, 6, 8, 10, or 12 hours, or some other time.

Figure 11:
FIG. 11 illustrates an example graphical user display according to specific embodiments of the present invention wherein, in addition to other data displayed, the display includes an indication of detected seizure events that persist on the screen for a period of time or optionally until cleared by a staff person according to specific embodiments of the invention In this figure, a heavy (e.g., red) bar is displayed at the bottom of the screen to indicate that a detected seizure event is taking place. This data can optionally be displayed along with some or all of the data shown in FIG. 10/

FIG. 11 illustrates an example graphical user display according to specific embodiments of the present invention wherein, in addition to other data displayed, the display includes an indication of detected seizure events that persist on the screen for a period of time or optionally until cleared by a staff person according to specific embodiments of the invention In this figure, a heavy (e.g., red) bar is displayed at the bottom of the screen to indicate that a detected seizure event is taking place.

Figure 12:
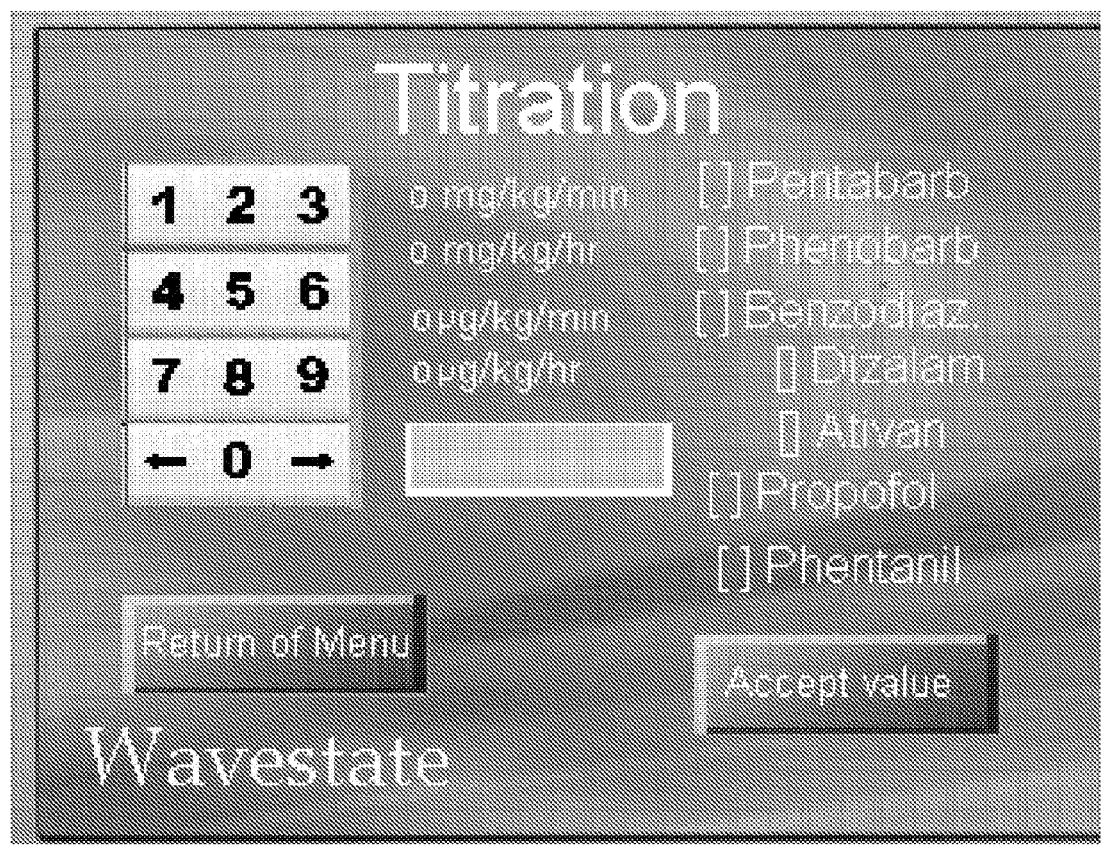
FIG. 12 illustrates an example graphical user interface allowing for input of titration values either for titration display calculation or optionally for automatic titration control according to specific embodiments of the invention.

FIG. 12 illustrates an example graphical user interface allowing for input of titration values either for titration display calculation or optionally for automatic titration control according to specific embodiments of the invention.

6. System Embodiments

In further embodiments, the invention may be incorporated in a device designed to maintain induced coma with statistical accuracy. The device reports the burst-suppression interval with statistical confidence to the staff in order to aid them in proper titration of hypnotics. In example applications, such a device will allow for controlled study of such issues as the maintenance of different interburst intervals (e.g., shorter such as 4 seconds versus longer, such as 12 seconds) as a test of patient outcome and the effectiveness of different hypnotics with accurate maintenance of the interval.

Software Implementations

Various embodiments of the present invention provide methods and/or systems for burst suppression monitoring that can be implemented on a general purpose or special purpose information handling appliance using a suitable programming language such as Java, C++, Cobol, C, Pascal, Fortran., PL1, LISP, assembly, etc., and any suitable data or formatting specifications, such as HTML, XML, dHTML, TIFF, JPEG, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

Embodiment in a Programmed Information Appliance

Figure 13:
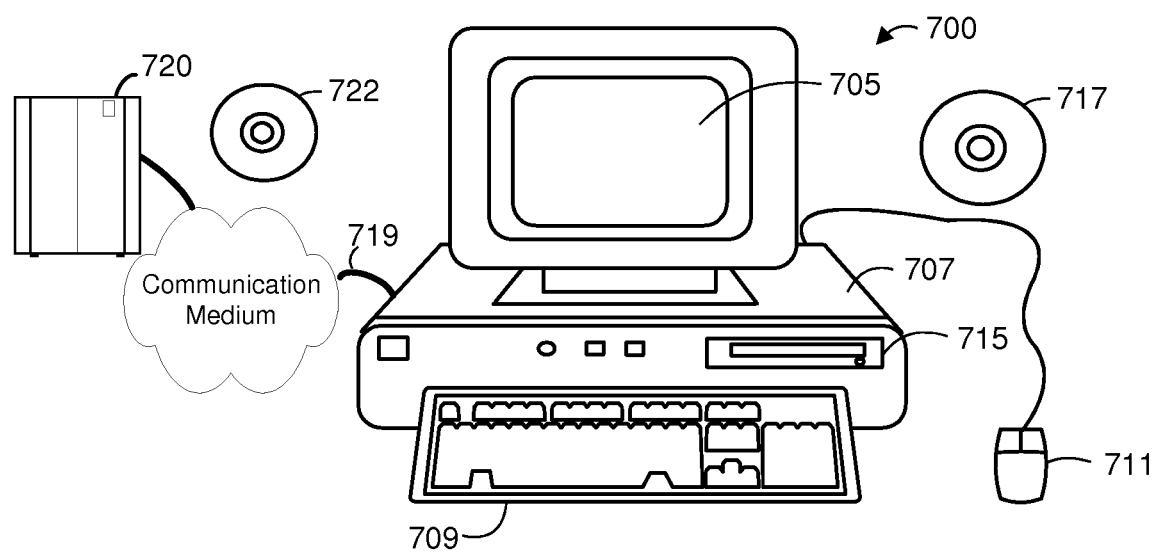
FIG. 13 is a block diagram showing a representative example logic device in which various aspects of the present invention may be embodied.

FIG. 13 is a block diagram showing a representative example logic device in which various aspects of the present invention may be embodied. As will be understood to practitioners in the art from the teachings provided herein, the invention can be implemented in hardware and/or software. In some embodiments of the invention, different aspects of the invention can be implemented in either a stand-alone device that includes just the BS monitoring functions described herein or in systems or devices that include any number of medical functions. As will be understood in the art, the invention or components thereof may be embodied in a fixed media program component containing logic instructions and/or data that when loaded into an appropriately configured information processing device cause that device to perform according to the invention. As will be understood in the art, a fixed media containing logic instructions may be delivered to a user on a fixed media for physically loading into a user's computer or a fixed media containing logic instructions may reside on a remote server that a user accesses through a communication medium in order to download a program component.

FIG. 13 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

7. Other Embodiments

The invention has now been described with reference to specific embodiments. Other embodiments will be apparent to those of skill in the art. In particular, a number of novel methods and apparatus have been described herein in the context of a novel method for monitoring subjects. It should be understood that the invention in specific embodiments encompasses any of these novel elements separately and used in any other suitable application. The invention also comprises the general methods that will be understood from the description herein. Thus, it is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

What is claimed:

1. A method of monitoring a sedated subject using a logic processor in a monitoring system comprising:
   receiving digital data representing said subject's EEG signal at said processor;
   using said processor to determine one or more burst onsets;
   using said processor to determine one or more suppression onsets;
   using said processor to determine one or more interburst or burst suppression intervals by comparing one or more burst onsets to one or more previous suppression onsets;
   using said processor to determine a true interburst interval or true mean burst suppression (BS) interval for a specified time length with statistical confidence wherein said mean burst suppression interval indicates time between burst onsets and previous suppression onsets, regardless of burst duration;
   using said mean burst suppression interval to inform therapy for said subject to maintain said desired state of sedation;
   calculating an absolute amplitude difference across said EEG signal, with an absolute amplitude difference history interval;
   smoothing said absolute amplitude difference to minimizes effects of signal variation on onset detection; and
   detecting burst onset when an absolute smoothed amplitude difference exceeds a median absolute amplitude times a specified multiplication factor.

2. The method of claim 1 further wherein:
   said using said mean burst suppression interval to inform therapy comprising presenting data indicating said mean burst suppression interval with statistical confidence to a user, thereby providing the user information to guide adjusting therapy to a subject to maintain the desired state of sedation.

3. The method of claim 1 further wherein:
   said using said mean burst suppression interval to indicate therapy comprising using a processor controlled medical device to adjust administration of one or more therapies using said mean burst suppression (BS) interval.

4. The method of claim 1 further wherein:
   said subject is being maintained in an induced coma and said method is used by an automated system to prevent over-sedation or under-sedation.

5. The method of claim 1 further comprising:
   using said processor to perform statistical analysis to correct for noise variability, other isoelectric variability, or other electric disturbances in said EEG.

6. The method of claim 1 further comprising:
   presenting data to a user indicating a true interburst interval with statistical accuracy.

7. The method of claim 1 further wherein:
   said digital data representing said subject's EEG is a stream of digital samples of amplitude values at different data capture time points;
   and determining burst or suppression onset further by a method comprising:
   computing changes in amplitude substantially at each data capture point;
   using said processor to perform a smoothing operation at each data capture point; and
   using said processor to perform threshold differentiation at each data capture point.

8. The method of claim 7 further comprising:
   using said processor to determine a possibility of an onset of burst or suppression for substantially each and every digital sample.

9. The method of claim 1 further wherein said method is embodied as an automatic computer-aided segmentation algorithm to improve patient care by guiding titration of sedatives.

10. The method of claim 1 further comprising:
    using said processor to pre-process said EEG signal data to perform noise reduction by mathematical smoothing operations such as smoothing and filtering; and
    further wherein said noise reduction comprising one or more of:
    using a 3-sample-skip comparison wherein amplitude at a time 0 is compared to amplitude at a time 3, amplitude at time 1 to amplitude at time 4, etc.;
    using a 1-sample skip to capture rare low-amplitude bursts in some patients;
    using a 2-sample skip as a default case.

11. The method of claim 1 further comprising:
    using data from one or more EEG channels to detect variance in BS generation across scalp recordings to strengthen reliability of detection of burst onset and suppression onset.

12. The method of claim 1 further comprising:
    calculating absolute amplitude difference ($d_i$) in microvolts continuously across said EEG signal, with a 1 second history;
    using smoothing to minimizes effects of signal variation on onset detection; and
    detecting burst onset when an absolute amplitude difference ($d_i$) exceeds 2 times a median (m) absolute amplitude.

13. The method of claim 12 further comprising:
    calculating said absolute amplitude difference ($d_i$) according to $$d_i = \frac{1}{R}\sum_{i=1}^{R}[A_i - A_{i-4}];$$

wherein A=amplitude of an EEG sample i; and
R indicates a number of samples in a time period.

14. The method of claim 1 further comprising:
    calculating absolute amplitude difference ($d_i$) in microvolts continuously across said EEG signal, with a 1 second history;
    using smoothing to minimizes effects of signal variation on onset detection to determine a; smoothed amplitude difference; and
    detecting burst onset when an absolute smoothed amplitude difference exceeds B times a median (m) absolute amplitude;

wherein B is chosen theoretically or empirically and can be adjusted per patient or learned by an algorithm for said subject.

15. The method of claim 12 further comprising:

determining a median absolute amplitude (MAA) from a longer running history;

updating said median absolute amplitude periodically.

16. The method of claim 1 further wherein:

said mean burst suppression interval is expressed in units of seconds.

17. The method of claim 1 further comprising:

using said processor to determine a statistical confidence value (P) of said mean burst suppression interval;

using said mean burst suppression interval along with said statistical confidence value to adjust therapy to a subject to maintain said desired state of sedation.

18. The method of claim 12 further comprising:

ignoring a particular suppression onset whenever a burst onset occurs less than a specified time (e.g., 500 or 1000 ms) after said particular suppression onset.

19. The method of claim 3 further comprising:

determining central tendency of burst onsets over a period of time and to a user presenting results in units of bursts per minute or mean burst interval in seconds or like measure of central tendency.

20. The method of claim 19 further comprising:

allowing a user to set a history over which said bursts per minute is measured;

using a default history duration if a user so indicates or does not select a different history.

21. The method of claim 12 further comprising:

resetting a time count (e.g., number of digitized samples since last burst onset) to zero at each burst onset, wherein a preceding immediately prior time count is designated a current burst suppression (BS) interval.

22. The method of claim 12 further comprising:

said mean burst suppression interval ($\bar{b}/R$) is expressed in units of seconds and is determined by said logic processor;

wherein R=sample rate/sec and b is determined according to:

$$\bar{b} = \frac{1}{n-1} \sum_{j=2}^{n} b_i;$$

wherein n=number of intervals collected;

wherein j=tally or count or array of number of intervals collected, $t_i = t_i + 1$;

t=time count since last burst;

wherein c is a variable indicating a classification of state as either burst or suppression;

wherein if $d_i/2 > m_i$, $c_i = 1$;

wherein if $d_i < m_i$, $c_i = 0$, else $c_i = c_{i-1}$;

wherein b may be computed linearly, or compressed such as natural log of digitized samples between offset and subsequent burst onset, or exponentially represented such as the square of the number of samples;

wherein if $c_i = c_{i-1}$ then if $t_{i-1} < R$, $c_i = c_{i-1}$ else if $t_{i-1} \geq R$, $b_j = b_{j+1}$, $b_j = t_{i-1}$, $t_i = 0$.

23. The method of claim 12 further comprising:

indicating confidence at 95% if $$\frac{s}{\sqrt{n}} > .166R$$

for 1 minute given the standard deviation of burst intervals and number of intervals;

wherein $$s = \sqrt{\frac{1}{n-1} \sum_{j=2}^{n} (b_j - \bar{b})^2},$$

where s=standard deviation, n=number of intervals.

* * * * *